United States Patent
Griesser et al.

(10) Patent No.: US 8,965,533 B2
(45) Date of Patent: Feb. 24, 2015

(54) DEFIBRILLATOR ELECTRODE PAD WITH TWO PEEL TABS

(75) Inventors: Hans Patrick Griesser, Bainbridge Island, WA (US); Christian James Richard, Shoreline, WA (US); Eric Grant Halsne, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/005,283

(22) PCT Filed: Mar. 20, 2012

(86) PCT No.: PCT/IB2012/051331
§ 371 (c)(1),
(2), (4) Date: Sep. 16, 2013

(87) PCT Pub. No.: WO2012/131536
PCT Pub. Date: Oct. 4, 2012

(65) Prior Publication Data
US 2014/0012360 A1 Jan. 9, 2014

Related U.S. Application Data

(60) Provisional application No. 61/468,164, filed on Mar. 28, 2011.

(51) Int. Cl.
*A61N 1/00* (2006.01)
*A61N 1/04* (2006.01)

(52) U.S. Cl.
CPC .................................. *A61N 1/046* (2013.01)
USPC ......................................................... 607/142

(58) Field of Classification Search
CPC ............................. A61N 1/046; A61N 1/3956
USPC ........................................................ 607/5, 142
See application file for complete search history.

(56) References Cited

U.S. PATENT DOCUMENTS

| 5,150,708 A | 9/1992 | Brooks |
| 5,362,420 A | 11/1994 | Itoh et al. |
| 6,272,385 B1 * | 8/2001 | Bishay et al. ................. 607/142 |
| 2006/0142805 A1 * | 6/2006 | Katzman et al. ................. 607/5 |

FOREIGN PATENT DOCUMENTS

| EP | 0983775 A2 | 3/2000 |
| WO | 2005092430 A1 | 10/2005 |

* cited by examiner

*Primary Examiner* — Christopher D Koharski
*Assistant Examiner* — Nadia A Mahmood

(57) ABSTRACT

An improved defibrillator electrode (100) has two separate peel tabs (114, 116). At least one of the peel tabs is located on the same edge of the electrode backing as that of the electrode wire. The disposition of the peel tabs improves the ability of the rescuer to apply the electrodes to a patient after the electrodes are removed from the release liner (110). In addition, the peel tab reduces the risk of damage to the electrode during removal from the release liner.

16 Claims, 5 Drawing Sheets

DEFIBRILLATOR ELECTRODE PAD WITH TWO PEEL TABS

CROSS-REFERENCE TO PRIOR APPLICATIONS

This application is the U.S. National Phase application under 35 U.S.C. §371 of International Application No. PCT/IB2012/051331, filed on Mar. 20, 2012, which claims the benefit of U.S. Provisional Patent Application No. 61/468,164, filed on Mar. 28, 2011. These applications are hereby incorporated by reference herein.

Aspects of this invention relate generally to electrodes for medical instruments, and more particularly to defibrillating/pacing devices or cardiac monitors with improved electrode pads that are easier to handle and apply to a patient.

Sudden cardiac death is the leading cause of death in the United States. Most sudden cardiac death is caused by ventricular fibrillation ("VF"), in which the muscle fibers of the heart contract without coordination, thereby interrupting normal blood flow to the body. The only known treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

One way of providing electrical defibrillation is by automatic or semiautomatic external defibrillators, collectively referred to as "AEDs," which analyze ECG signals from the heart and, upon detection of a treatable arrhythmia, sends electrical pulses to a patient's heart through electrodes applied to the torso to defibrillate the patient or to provide for external pacing of the patient's heart. The use of AEDs by untrained or minimally trained operators for a patient in sudden cardiac arrest is a time critical operation. The electrical pulse must be delivered within a short time after onset of VF in order for the patient to have any reasonable chance of survival.

The reception of the patient's ECG signals and the application of the appropriate therapeutic pulses or currents is done through conductive pads or electrodes applied to the patient's torso and connected to the AED base unit. Some AEDs are stored with electrodes that are pre-connected to the base unit in order to simplify deployment during a rescue. These types of AEDs ideally require only that the operator turn on the AED, peel the electrodes from their release liner, and apply them to the patient. The AED then analyzes the patient's ECG, arms the device for a defibrillating shock if necessary, and advises the operator to press the shock button.

Electrodes typically comprise a non-conductive base layer such as a plastic disc and a conductive layer that distributes the current transmitted to the electrode by the AED base unit. The non-conductive base layer is typically constructed of a thin, flexible polymeric material such as urethane foam, or a polyester or polyolefin laminate which is electrically insulating and provides structural integrity to the electrode. Conventionally, such electrodes further include a layer of adhesive material that is used to adhere the electrode to the patient's chest prior to and during delivery of the shocks. The adhesive material is typically a viscous water-based gel material that contains ionic compounds which increase the electrical conductivity of the material to provide a low resistance path for current to flow from the electrode to the patient's chest.

Electrodes used with automatic external defibrillators often are stored for relatively long periods of time until needed. During this time, the adhesive material can become desiccated. Desiccation decreases the effectiveness of the adhesive material in that it lowers the material's conductivity, which in turn raises the impedance at the contact area between the electrode and the skin. This increased impedance results in less current reaching the heart. Due to the problem of desiccation, the adhesive material is typically sealed away from the environment in a moisture-impervious enclosure. For example, the DP-style electrodes manufactured by Philips Healthcare, Andover Mass., are stored inside a sealed foil pouch, the electrode adhesive material disposed in contact with a release liner inside the pouch. A user tears the pouch open, removes the electrodes, and peels the electrode from the release liner. Because the DP-style electrodes have no need for any peel tab, the user holds the electrode wire for these functions.

Another form of electrode packaging which combines the benefits of pre-connection and long shelf-life is described in co-pending and co-assigned U.S. patent application Ser. No. 10/599,113 entitled "Self-Storing Medical Electrodes", which is incorporated herein by reference. FIG. 1 illustrates this electrode design. In this design each electrode comprises a flexible and moisture-impervious barrier layer 14 which is heat sealed to a rigid release liner 22 around its periphery 25. The conductive gel layer 18 of each electrode is sealed within the enclosure formed by the barrier layer 14, heat-seal, and rigid release liner 22, and is thus protected from desiccation. An electrode wire 40 is attached through the barrier layer 14 by means of a rivet 42 to a conductive foil layer 16 which resides between the barrier layer 14 and the gel layer 18. Peel tab 14' is meant to be used to peel the electrode away from the release liner. Often, however, the rescuer is motivated by the urgency of the rescue to pull directly on the electrode wire 40 which is connected on the opposite end from the peel tab 14' to remove the electrode from the release liner.

One potential problem arises because there is no tab at the wire end of the electrode for holding the electrode after peeling. Although there is a small area 38 under barrier layer 14 and wire 40 that does not have adhesive, the area 38 is not visible to the user prior to electrode deployment, and so the user will avoid grasping the electrode by that edge. Also, if the user is familiar with prior art electrodes having no peel tab, they may have become accustomed to peeling the electrode from the release liner by pulling on the electrode wire. For both of these reasons, it is likely that the user will hold the peeled-off electrode by the wire at the wire end. This makes the electrode more difficult and awkward to apply to the patient.

Another potential problem arises when the electrode wire 40 is used to peel the electrode away from the release liner 22. FIG. 5A shows that when the wire 40 is pulled, there is little or no peeling action. Instead, the heat seal between release liner 22 and barrier layer 14 is subject to substantial tensile stress across the entire adhesion area. The force required to break the seal is consequently very large, making it difficult for the user to deploy the electrode. Damage to the electrode can also occur under such large pulling force if the barrier layer 14 consequently fails at a different location than the intended heat seal interface.

In accordance with the principles of the present invention, an improved electrode and electrode assembly is provided which ameliorates the problems of handling and potential damage during deployment of the electrode for use. An electrode backing layer is described which comprises a second peel tab located at the wire end of the electrode. The second peel tab is intuitive for the user to grasp during the urgency of a cardiac rescue. By grasping both the first and second peel tabs during deployment, the rescuer can adhere the electrode to the patient's torso with greater ease and accuracy.

In accordance with a further aspect of the present invention, an electrode with a peel tab disposed immediately below the electrode wire is provided. The peel tab is also intuitive to grasp for peeling instead of the electrode wire. Use of the peel tab reduces the force required to peel the electrode from the release liner substantially, and also avoids potential damage to the electrode itself.

In accordance with yet another aspect of the present invention, an electrode peel tab is disposed in contact with the electrode lead wire. The peel tab and lead wire are bonded together such that if the wire is pulled to peel the electrode from the release liner, the peel tab serves as a strain relief for the electrode. Acting as a shear element from electrode lead wire to heat seal area, the peel tab lifts the edge of the heat seal instead of subjecting the entire area to tensile forces. Thus, easy peeling with no damage to the electrode is assured.

IN THE DRAWINGS

Figure 1:
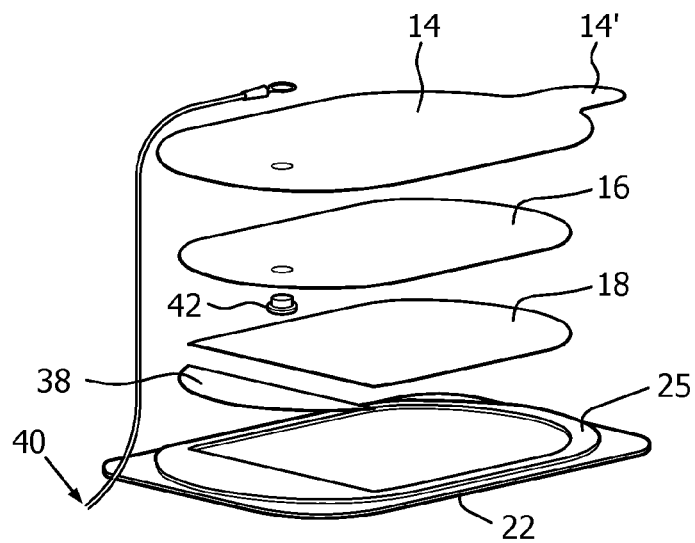
FIG. 1 illustrates an existing defibrillator electrode having a moisture impervious barrier enclosure formed by a flexible electrode backing layer heat sealed to a rigid release liner.
Figure 2:
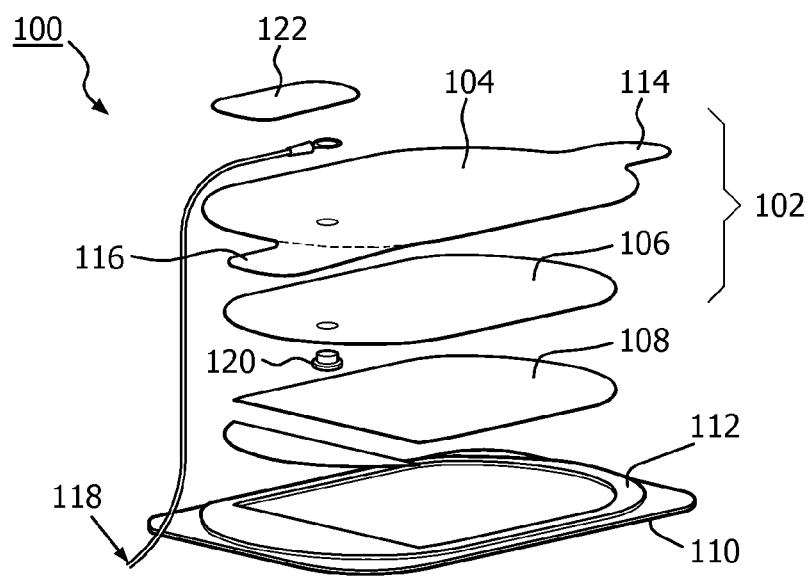
FIG. 2 is an illustration of a medical electrode of the present invention, comprising two peel tabs at generally opposite ends the electrode.

FIG. 2 illustrates one embodiment of the present invention. An electrode 100 comprises a flexible electrode body 102 and a conductive gel layer 108. Electrode body 102 is comprised of a flexible and moisture-impervious barrier layer 104 bonded to a conductive layer 106. Conductive layer 106 is disposed in electrical contact with conductive gel layer 108. An electrode lead wire 118 is attached to the conductive layer 106 through the barrier layer 104 by means of a rivet 120. Rivet 120 provides a moisture impervious seal through the rivet hole in barrier layer 104.

Electrode body 102 is heat sealed to a rigid release liner 110 at the heat seal periphery 112. The conductive gel layer 108 is thus sealed within the enclosure formed by the barrier layer 104, heat-sealing material, and rigid release liner 110, and is thus protected from desiccation.

Barrier layer 104 further comprises two peel tabs. A first peel tab 114 is disposed on one end of flexible barrier material 104. A second peel tab 116 is disposed on a generally opposite end of flexible barrier material 104 from the first peel tab 114. Second peel tab 116 is configured such that it is intuitive to grasp the second peel tab 116 instead of lead wire 118 to peel the electrode 100 from the release liner 110. Such configuration of peel tab 116 could extend to sizing larger and longer than peel tab 114, distinctive coloration, or placing graphic instructions thereon.

Preferably, second peel tab 116 is co-located with lead wire 118 adjacent the connection to rivet 120. In addition, second peel tab 116 may be affixed to lead wire 118 with optional strain relief tab 122. Strain relief tab 122 serves to improve the electrode peeling action from the wire end of electrode body 102, as will be explained in further detail below. Strain relief tab 122 should be comprised of a material that is resistant to tearing. Strain relief tab 122 may be adhesively bonded to second peel tab 116 and lead wire 118, or may otherwise provide some attaching structure to, such as weaving, between the second peel tab 116 and lead wire 118. Alternatively, strain relief tab 122 may be comprised solely of an adhesive which bonds second peel tab 116 to lead wire 118.

Materials and manufacturing methods that may be used for constructing electrode body 102, gel layer 108, release liner 110, rivet, and heat sealing are described in co-pending and co-assigned U.S. patent application Ser. No. 10/599,113. In addition, either of peel tabs 114, 116 may be integrally formed with flexible barrier material 104 or may be separate components which are bonded to flexible barrier material 104 during manufacturing. If separately bonded to barrier material 104, second peel tab 116 may additionally be disposed overlying lead wire 118 and/or rivet 120.

To deploy the stored electrodes for use in a cardiac emergency, the user may grasp first peel tab 114 to peel the electrode away from release liner 110. The user may also or alternatively grasp second peel tab 116 to peel the electrode away from release liner 110 for use. After removing electrode 100 from release liner 110, the user guides the electrode to the proper placement on the patient's torso by use of holding both peel tabs. This control is thus improved over the prior art one-peel-tab or no-peel-tab electrodes.

Figure 5A:
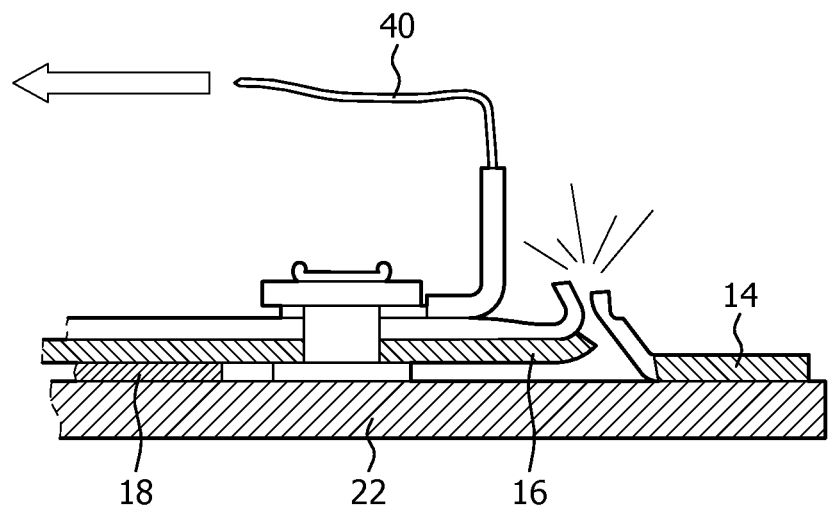
FIG. 5A illustrates the result of using the electrode wire in an existing defibrillator electrode to peel the electrode from the release liner.
Figure 5B:
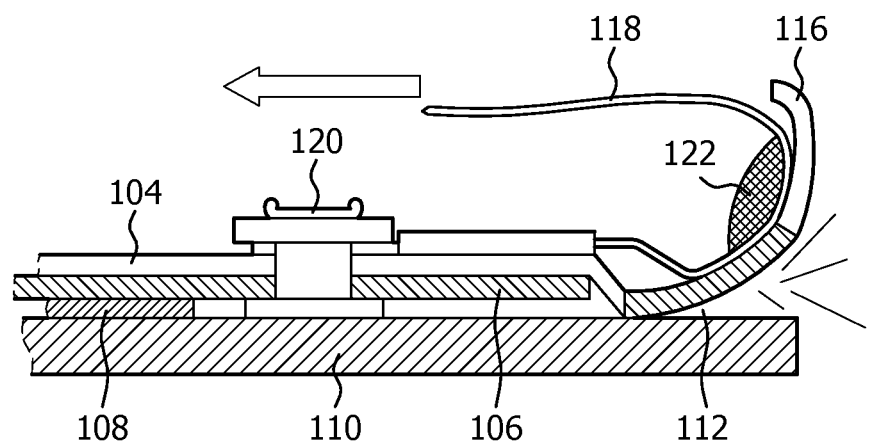
FIG. 5B illustrates the improved result of using the electrode wire in the inventive defibrillator electrode to peel the electrode from the release liner.

In the event that the user grasps lead wire 118 to peel the electrode 100 from the release liner 110, the optional strain relief tab 122 protects the electrode 100 from damage. As can be seen in FIG. 5B, a pull on lead wire 118 lifts second peel tab 116 as well by means of strain relief tab 122. As the second peel tab 116 rotates away from release liner 110, the bond at heat seal periphery 112 experiences a gradual lifting force, starting at the outer extent of the bond. As can be seen in FIG. 5B, no part of the electrode body 104, 106 or rivet 120 is stressed under this configuration. Thus in addition to enabling substantially less peeling force, strain relief tab 122 also prevents potential damage to the electrode.

Figure 3:
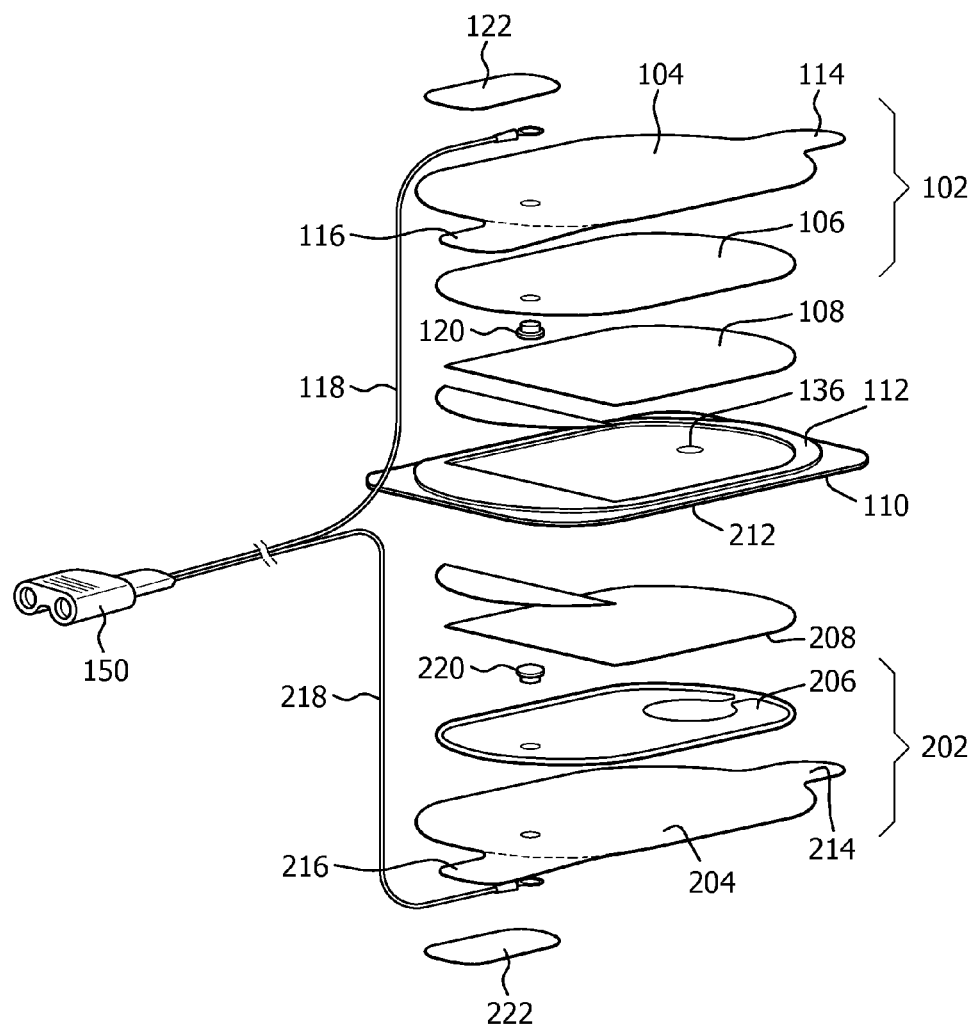
FIG. 3 illustrates a self-storing medical electrode system of the present invention, comprising two electrodes sealed to opposite sides of a rigid release liner, each electrode comprising at least one peel tab disposed at the electrode wire end.

FIG. 3 illustrates one embodiment of an electrode system comprising a pair of electrodes disposed on each side of a single substantially rigid non-conductive release liner 110. The resulting assembly is easy to store and to use, and minimizes the detritus generated during the cardiac emergency.

Each of the FIG. 3 electrodes is constructed similarly to electrode 100 as described previously and as shown in FIG. 2. In particular, each of the pair of electrodes comprises an electrode body 102, 202 having first and second sides, wherein the first side comprises a flexible moisture barrier layer 104, 204 having a sealable periphery and the second side comprises a conductive layer 106, 206. Each electrode further comprises an electrically conductive gel layer 108, 208 interposed between the conductive layer 106, 206 and the non-conductive release liner 110. Each gel layer 108, 208 is in electrical contact with its respective conductive layer 106, 206. Each moisture barrier layer 104, 204 is sealed at its sealable periphery to a corresponding sealing surface 122, 212 on release liner 110, such that a hermetic seal is formed between each gel layer 108, 208 and the outside environment.

Each electrode conductive layer 106, 206 is connected to a lead wire 118, 218 through the first side by means of a rivet 120, 220. Rivets 120, 220 provide a moisture impervious seal through the rivet hole in barrier layers 104, 204. The other end of each lead wire 118, 218 is connected to a device connector 150. Connector 150 is shaped to provide an electrical connection to a medical device such as a defibrillator.

Rigid release liner 110 may optionally comprise a conductive element 136 which provides a conductive path through the thickness of the release liner. With the electrodes affixed to the release liner 110, it can be seen by FIG. 3 that an electrical circuit is formed from connector 150 via lead wire 118, conductive layer 106, gel layer 108, conductive element 136, gel layer 208, conductive layer 206, and lead wire 218 back to connector 150. This circuit can be used by the attached defibrillator to sense the condition of the adhesive gel and to sense when one of the electrodes has been removed from the release liner 110.

FIG. 3 also illustrates that each electrode has a first peel tab 114, 214 disposed on the periphery of the electrode body on a first end, and a second peel tab 116, 216 disposed on the periphery of its respective electrode body on a second end. The peel tabs may be formed as part of their respective backing layer 104, 204, or may be formed as separate pieces and applied to the backing layer 104, 204 during manufacturing. Each second peel tab 116, 216 may be optionally affixed to its respective lead wire 118, 218 by strain relief tab 122, 222 in a means similar to that described previously for the FIG. 2 embodiment.

Figure 4B:
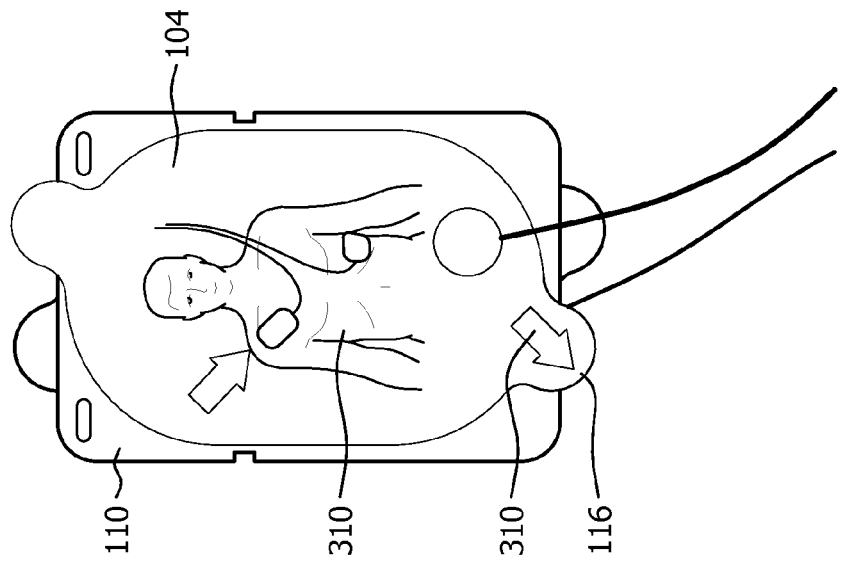
FIG. 4B is an illustration of a different embodiment of the self-storing medical electrode system of FIG. 3, in an assembled state and showing a user graphic on the electrode surface.
Figure 4A:
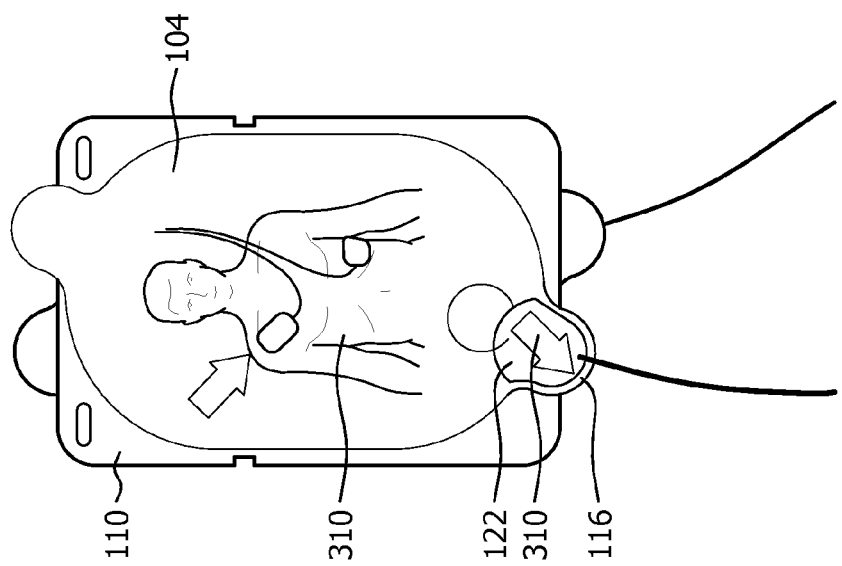
FIG. 4A is an illustration of the self-storing medical electrode system of FIG. 3, in an assembled state and showing a user graphic on the electrode surface.

FIG. 4a illustrates an embodiment of the assembled FIG. 3 electrode system, further showing the appearance of the system to the user. In this embodiment, a graphic 310 depicting the proper placement of the electrode on the patient is placed on the barrier layer 104. Graphic 310 also highlights the second peel tab 116 to the user, to encourage the use of the second peel tab 116 instead of the lead wire in peeling. A similar graphic depicting the proper placement of the other electrode may be placed on the electrode residing on the back side of release liner 110. Graphic 310 may further be printed over strain relief tab 122 if it is used.

FIG. 4b illustrates a different embodiment of the assembled FIG. 3 electrode system. This embodiment illustrates the configuration in which the second peel tab 116 is co-located with, but does not underlie, the electrode lead wire. Graphic 310, placed on barrier layer 104, similarly depicts the proper placement of the electrode on the patient. Graphic 310 also highlights the second peel tab 116 to the user to encourage the use of the second peel tab 116 instead of the lead wire in peeling. A similar graphic depicting the proper placement of the other electrode may be placed on the electrode residing on the back side of release liner 110.

Figure 6:
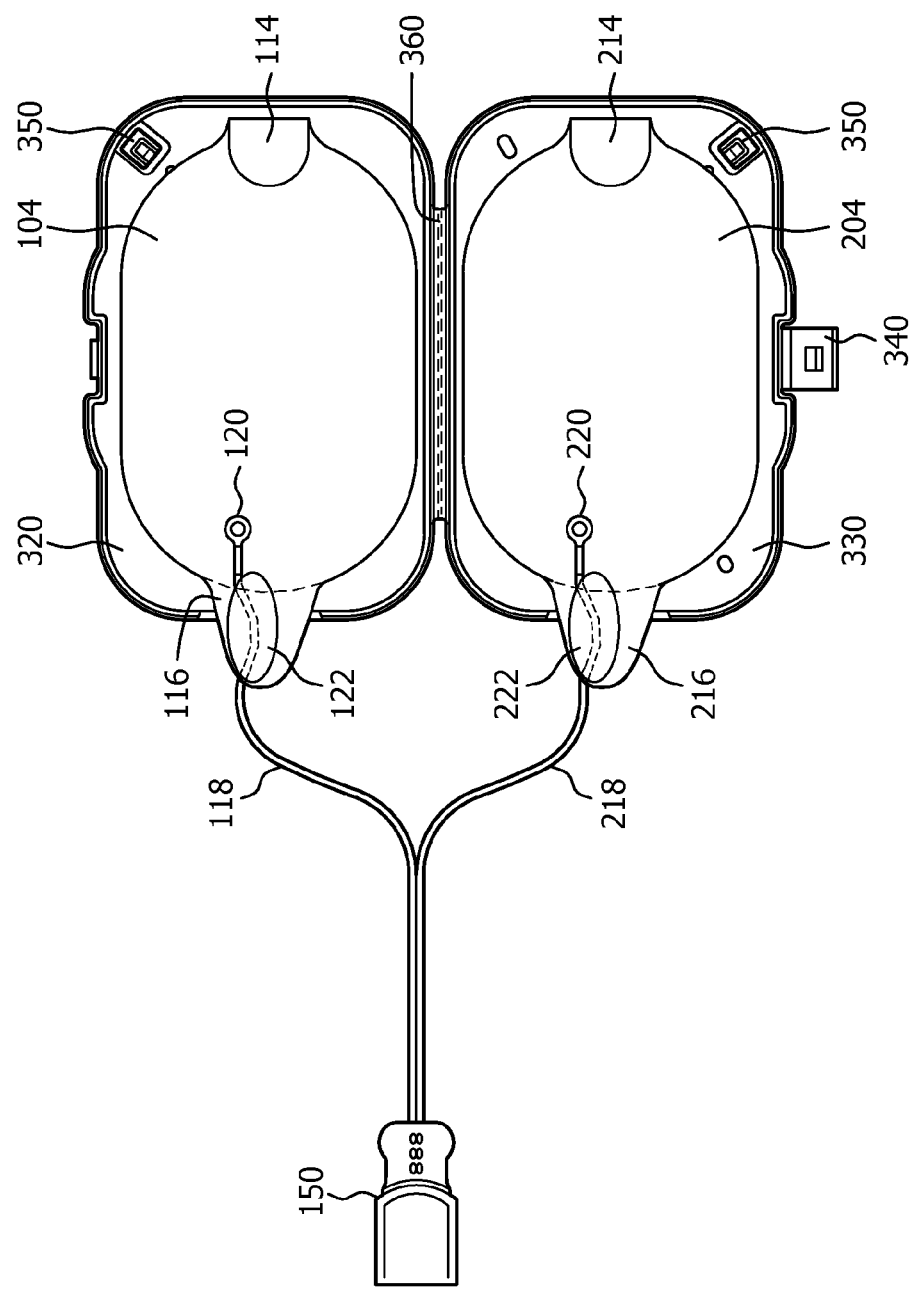
FIG. 6 illustrates an alternate embodiment of a self-storing medical electrode system of the present invention, comprising two electrodes sealed to the same side of a clamshell-type rigid release liner, each electrode comprising at least one pull tab disposed at the electrode wire end.

Alternate arrangements of the electrodes and the electrode system of FIG. 3 are envisioned which fall within the scope of the claimed invention. For example, FIG. 6 illustrates an alternate embodiment of a self-storing medical electrode system of the present invention, comprising two electrodes sealed to the same side of a clamshell-type rigid release liner. Each electrode is configured similarly to the electrodes described previously and shown in FIG. 2 and FIG. 3. The FIG. 6 release liner is comprised of two clamshell release liner halves 320, 330, which may be hingeably attached by a clamshell hinge 360. The release liner assembly may be closed about the hinge 360 and clasped shut with clamshell clasp 340 to protect the electrodes stored inside.

The FIG. 6 embodiment further comprises electrodes sealed about their periphery of flexible backing layers 104, 204 to their respective clamshell half 320, 330. Each lead wire 118, 218 and optionally a portion of second peel tab 116, 216 extends through a gap in the clamshell halves for connection at connector 150 to a defibrillator device. Finally, conductive element 350 is comprised of two parts which conductively connect together when the clamshell is closed. Each conductive element further comprises a path to the conductive layer underlying flexible backing layers 104, 204. Thus is formed an electrode status circuit similar to that described in FIG. 3.

| Number | Name |
|---|---|
| 14 | barrier layer - prior art |
| 14' | Peel tab - prior art |
| 16 | foil layer - prior art |
| 18 | gel layer - prior art |
| 22 | rigid release liner - prior art |
| 25 | Heat seal periphery - prior art |
| 38 | area - prior art |
| 40 | electrode wire - prior art |
| 42 | rivet - prior art |
| 100 | electrode |
| 102 | Electrode body |
| 104 | Flexible barrier layer |
| 106 | Conductive layer |
| 108 | Gel layer |
| 110 | Release liner |
| 112 | Heat seal periphery |
| 114 | First peel tab |
| 116 | Second peel tab |
| 118 | lead wire |
| 120 | Rivet |
| 122 | Strain relief tab |
| 136 | Conductive element |
| 150 | Electrode connector |
| 200 | Electrode system |
| 202 | Second Electrode body |
| 204 | Second Electrode Flexible barrier layer |
| 206 | Second Electrode Conductive layer |
| 208 | Second Electrode gel layer |
| 212 | Second Electrode Heat seal periphery |
| 214 | Second Electrode First peel tab |
| 216 | Second Electrode Second peel tab |
| 218 | Second Electrode lead wire |
| 220 | Second Electrode Rivet |
| 222 | Second Electrode Strain relief tab |
| 300 | Alternate Electrode System |
| 310 | Graphic |
| 320 | Clamshell release liner first half |
| 330 | Clamshell release liner second half |
| 340 | Clamshell clasp |
| 350 | Clamshell conductive element |
| 360 | Clamshell hinge |

What is claimed is:

1. An electrode comprising:
an electrode body having a first and second side, wherein the first side comprises a flexible barrier layer comprising a heat-sealable material and the second side comprises a conductive layer;
a lead wire that is connected to the flexible barrier layer of the electrode body on the second end and which electrically connects the electrode to a medical device via a path from the first side to the second side of the electrode body
an electrically conductive gel layer disposed on the electrode body and which is further in electrical communication with the conductive layer;
a release liner sealed to said flexible barrier layer around a periphery of said gel layer;
a first peel tab disposed on the periphery of the electrode body on a first end;

a second peel tab disposed on the periphery of the electrode body on a second end; and a strain relief tab which bonds the second peel tab to the lead wire in a configuration that releases strain between the lead wire and the flexible barrier layer.

2. The electrode of claim 1, wherein the lead wire is further disposed overlying the second peel tab and the flexible barrier layer.

3. The electrode of claim 1, wherein the second peel tab is integral to the flexible barrier layer.

4. The electrode of claim 1, wherein the second peel tab is adhesively bonded to the flexible barrier layer.

5. The electrode of claim 1, further comprising a graphic printed on the flexible barrier layer first side for providing electrode application instruction to a user.

6. The electrode of claim 1, wherein said release liner is substantially rigid.

7. An electrode system comprising:

a substantially rigid non-conductive release liner; and a pair of electrodes disposed on the non-conductive release liner, wherein each electrode comprises, an electrode body having first and second sides, wherein the first side comprises a flexible moisture barrier layer having a sealable periphery and the second side comprises a conductive layer, an electrically conductive gel layer interposed between the conductive layer and the non-conductive release liner, a first peel tab disposed on the periphery of the electrode body on a first end, and a second peel tab disposed on the periphery of the electrode body on a second end, and a lead wire that is connected through said first side to said second side of the electrode at the second end and which electrically connects the electrode to a medical device, and a strain relief tab which bonds it respective second peel tab to the lead wire in a configuration that releases strain between the lead wire and the flexible barrier layer, wherein the periphery of the moisture barrier layer of each electrode is sealed to the release liner to form a hermetic seal between each gel layer and the outside environment.

8. The electrode system of claim 7, wherein the electrodes are further disposed on opposite sides of the non-conductive release liner, and further wherein the pair of electrodes are in electrical contact with each other through a conductive element that is disposed within the non-conductive release liner and which is in electrical contact with both electrodes through said gel layer.

9. The electrode system of claim 7, wherein on each electrode the lead wire is further disposed overlying the second peel tab and the flexible barrier layer.

10. The electrode of claim 7, wherein on each electrode the second peel tab is integral to the flexible barrier layer.

11. The electrode of claim 7, wherein on each electrode the second peel tab is adhesively bonded to the flexible barrier layer.

12. The electrode of claim 7, further comprising a graphic printed on the flexible barrier layer first side of each electrode for providing electrode application instruction to a user.

13. A method of applying an external defibrillator electrode to a patient, comprising the steps of:

providing a substantially rigid release liner;

providing an electrode body having a first and second side, wherein the first side comprises a flexible barrier layer comprising a heat-sealable material and the second side comprises a conductive layer, an electrically conductive gel layer disposed on the electrode body and which is further in electrical communication with the conductive layer, a first peel tab disposed on the periphery of the electrode body on a first end, and a second peel tab disposed on the periphery of the electrode body on a second end, wherein the release liner is sealed to said flexible barrier layer around a periphery of said gel layer;

providing a lead wire that is connected to the flexible barrier layer of the electrode body on the second end and that is adhesively connected to the second peel tab, and which electrically connects the electrode to a medical device via a path from the first side to the second side of the electrode body;

removing the electrode body from the release liner by breaking the seal with the second peel tab;

grasping the electrode body on the first peel tab and the second peel tab; and adhesively applying the electrode body gel layer to the patient's skin.

14. The method of claim 13, further comprising the step of pulling on the lead wire prior to the removing step.

15. The method of claim 14, wherein the step of pulling strains the second peel tab in order to break the seal.

16. The method of claim 13, wherein the removing step further comprising breaking the seal by direct pull on the second peel tab.

* * * * *